(12) United States Patent
Zhang et al.

(10) Patent No.: US 8,145,307 B2
(45) Date of Patent: Mar. 27, 2012

(54) METHOD AND APPARATUS FOR ENHANCING TREATABLE ARRHYTHMIA DETECTION SPECIFICITY BY USING ACCUMULATED PATIENT ACTIVITY

(75) Inventors: Xusheng Zhang, Shoreview, MN (US); Raja N. Ghanem, Edina, MN (US); Robert W. Stadler, Shoreview, MN (US); Paul G. Krause, Shoreview, MN (US); Karen J. Kleckner, New Brighton, MN (US)

(73) Assignee: Medtronic, Inc., Minneapolis, MN (US)

( * ) Notice: Subject to any disclaimer, the term of this patent is extended or adjusted under 35 U.S.C. 154(b) by 106 days.

(21) Appl. No.: 12/869,180

(22) Filed: Aug. 26, 2010

(65) Prior Publication Data

US 2012/0053477 A1 Mar. 1, 2012

(51) Int. Cl.
*A61N 1/365* (2006.01)
(52) U.S. Cl. .......................... 607/19; 600/515
(58) Field of Classification Search .................... 607/19; 600/515

See application file for complete search history.

(56) References Cited

U.S. PATENT DOCUMENTS

| | | | |
|---|---|---|---|
| 5,259,387 A | 11/1993 | dePinto |
| 5,948,005 A | 9/1999 | Valikai |
| 6,449,508 B1 | 9/2002 | Sheldon |
| 6,539,249 B1 | 3/2003 | Kadhiresan |
| 6,912,414 B2 | 6/2005 | Tang |
| 7,117,035 B2 | 10/2006 | Wagner |
| 7,130,686 B1 | 10/2006 | Levine |
| 7,171,271 B2 | 1/2007 | Koh |
| 7,210,240 B2 | 5/2007 | Townsend |
| 7,313,440 B2 | 12/2007 | Miesel |
| 7,395,113 B2 | 7/2008 | Heruth |
| 2006/0036288 A1 | 2/2006 | Bocek |
| 2007/0156190 A1 | 7/2007 | Cinbis |
| 2008/0177355 A1 | 7/2008 | Miesel |
| 2008/0270188 A1 | 10/2008 | Garg |

*Primary Examiner* — Michael Kahelin
(74) *Attorney, Agent, or Firm* — Michael C. Soldner

(57) ABSTRACT

A method and apparatus for detecting a cardiac event in a medical device determine an activity level count from an activity sensor signal for each of a number of time segments, store an activity level count for each of the time segments in a histogram, and accumulate the stored activity level counts to determine a percentage of time segments having an activity level count above a given activity level count.

23 Claims, 7 Drawing Sheets

METHOD AND APPARATUS FOR ENHANCING TREATABLE ARRHYTHMIA DETECTION SPECIFICITY BY USING ACCUMULATED PATIENT ACTIVITY

TECHNICAL FIELD

The present disclosure relates generally to an implantable medical device system, and more particularly to a method and apparatus for detecting arrhythmias using accumulated patient activity.

BACKGROUND

Many types of implantable medical devices (IMDs) have been implanted that deliver relatively high-energy cardioversion and/or defibrillation shocks to a patient's heart when a malignant tachyarrhythmia, e.g., ventricular tachycardia or ventricular fibrillation, is detected. Cardioversion shocks are typically delivered in synchrony with a detected R-wave when fibrillation detection criteria are met, whereas defibrillation shocks are typically delivered when fibrillation criteria are met and an R-wave cannot be discerned from the electrogram (EGM).

Implantation of an ICD commonly uses a transvenous approach for cardiac electrodes and lead wires. The defibrillator housing or "can" is generally implanted as an active "can" electrode for defibrillation and electrodes positioned in the heart are used for pacing, sensing and detection of arrhythmias.

Patients may be asymptomatic by conventional measures but are nevertheless at risk of a future sudden death episode and are candidates for a prophylactic implantation of a defibrillator (often called primary prevention). One option proposed for this patient population is to implant a prophylactic subcutaneous implantable device (SubQ device) that does not require leads to be placed in the bloodstream. Accordingly, complications arising from leads placed in the cardiovasculature environment are eliminated. Further, endocardial lead placement may not be advised for all patients. For example some patients who have a mechanical heart valve implant or pediatric cardiac patients may be contraindicated for endocardial lead placement. For these and other reasons, a SubQ device may be preferred over an ICD for some patients.

There are technical challenges associated with the operation of a SubQ device because the SubQ device is limited to far-field sensing of cardiac signals (ECG signals) since there are no intracardiac or epicardial electrodes in a subcutaneous system. For example, SubQ device sensing is challenged by the presence of muscle noise, motion artifact, respiration and other physiological and/or non-physiological signal sources. The SubQ device needs to sense low amplitude fibrillation waves for detecting fibrillation without oversensing muscle noise or other artifact. False detection of a treatable cardiac rhythm can lead to unnecessary arrhythmia therapies, such as cardioversion/defibrillation shocks which can be painful to the patient and use considerable battery energy.

Therefore, for these and other reasons, a need exists for an improved method and apparatus to reliably sense and detect treatable arrhythmias, while rejecting noise, motion artifact, and other physiologic and/or non-physiologic signals.

BRIEF DESCRIPTION OF THE DRAWINGS

Aspects and features of the method and apparatus disclosed herein will be appreciated as the same becomes better understood by reference to the following detailed description of various embodiments when considered in connection with the accompanying drawings, wherein.

DETAILED DESCRIPTION

Figure 1:
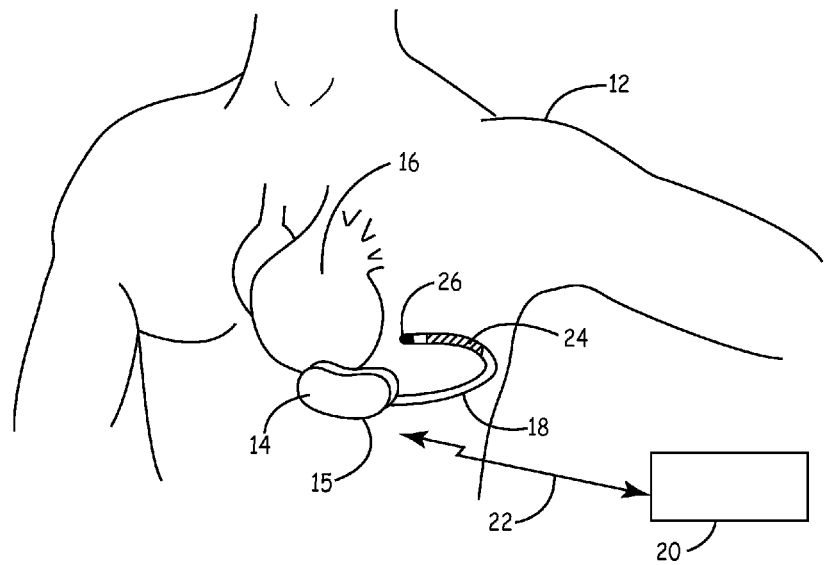
FIG. 1 and FIG. 2 are schematic diagrams of a subcutaneous device in which methods described herein may be usefully practiced.
Figure 2:
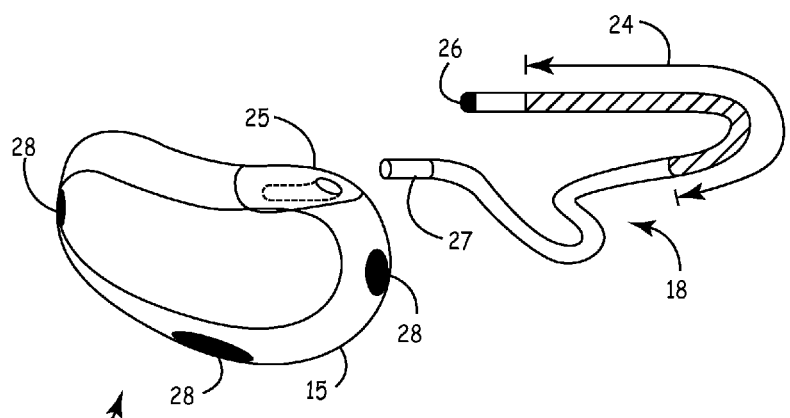

FIG. 1 and FIG. 2 are schematic diagrams of a subcutaneous device in which methods described herein may be usefully practiced. As illustrated in FIG. 1, a subcutaneous device 14 according to one embodiment is subcutaneously implanted outside the ribcage of a patient 12, anterior to the cardiac notch. Subcutaneous device 14 includes a housing 15 to enclose electronic circuitry of the device 14.

A subcutaneous sensing and cardioversion/defibrillation therapy delivery lead 18 in electrical communication with subcutaneous device 14 is tunneled subcutaneously into a location adjacent to a portion of a latissimus dorsi muscle of patient 12. Specifically, lead 18 is tunneled subcutaneously from the median implant pocket of the subcutaneous device 14 laterally and posteriorly to the patient's back to a location opposite the heart such that the heart 16 is disposed between the subcutaneous device 14 and the distal electrode coil 24 and distal sensing electrode 26 of lead 18.

It is understood that while the subcutaneous device 14 may be positioned between the skin and muscle layer of the patient, the term "subcutaneous device" is intended to include a device and any associated leads that can be positioned in any non-intravenous location of the patient, such as below the muscle layer or within the thoracic cavity, for example.

Further referring to FIG. 1, a programmer 20 is shown in telemetric communication with subcutaneous device 14 by an RF communication link 22. Communication link 22 may be any appropriate RF link such as Bluetooth, WiFi, or Medical Implant Communication Service (MICS).

Subcutaneous lead 18 includes a distal defibrillation coil electrode 24, a distal sensing electrode 26, an insulated flexible lead body and a proximal connector pin 27 (shown in FIG. 2) for connection to subcutaneous device 14 via a connector 25. In addition, one or more electrodes 28 (shown in FIG. 2) are positioned along the outer surface of the housing to form a housing-based subcutaneous electrode array (SEA). Distal sensing electrode 26 is sized appropriately to match the sensing impedance of the housing-based subcutaneous electrode array. It is understood that while device 14 is shown with electrodes 28 positioned on housing 15, electrodes 28 may be alternatively positioned along one or more separate leads connected to device 14 via connector 25.

The SubQ device 14 shown in FIGS. 1 and 2 is one illustrative embodiment of the type of device that may be adapted for practicing methods described herein. A SubQ device, as discussed above, is subject to muscle noise and motion artifact due to the subcutaneous placement or electrodes. As such the methods described herein are well-suited to address the type of muscle noise and/or motion artifact caused by patient activity that may interfere with accurate cardiac event detection. The methods described herein, however, may be implemented in other types of implantable devices configured to detect cardiac arrhythmias, including ICDs coupled to transvenous leads. As such, use of the term "ICD" hereafter is intended to include any device configured to detect cardiac arrhythmias, including those using transvenous electrodes or subcutaneous electrodes, or any combination thereof.

In the illustrative embodiments described herein, the disclosed methods are described in conjunction with an ICD capable of delivering a therapy in response to arrhythmia detection. In alternative embodiments, cardiac event detection methods described herein may be implemented in a monitoring device that does not include therapy delivery capabilities, such as an ECG recording device or an implantable cardiac hemodynamic monitor.

Figure 3:
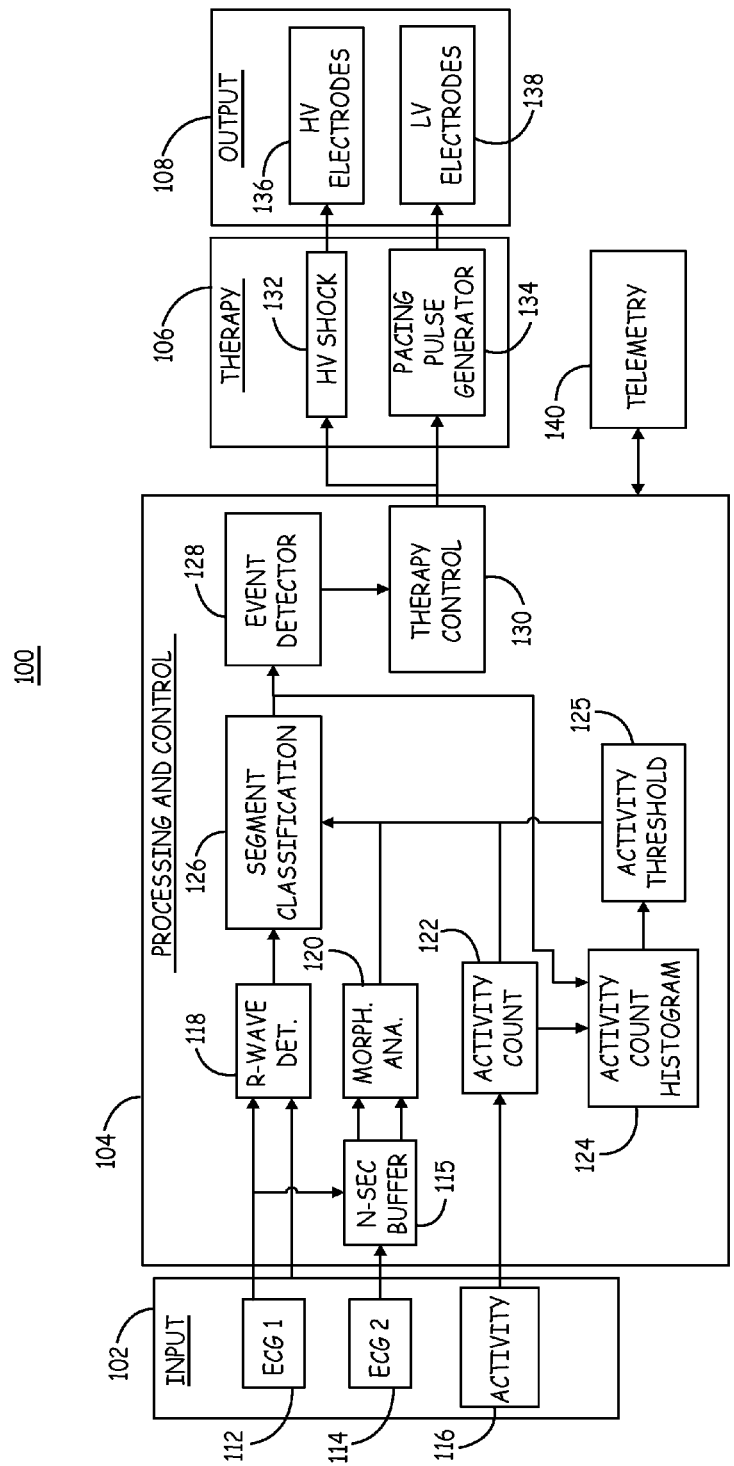
FIG. 3 is a functional block diagram of electronic circuitry that is included in one embodiment of an ICD for practicing the methods described herein.

FIG. 3 is a functional block diagram 100 of electronic circuitry that is included in one embodiment of an ICD for practicing the methods described herein. The ICD 100 includes input 102, processing and control 104, therapy module 106, output 108 and telemetry module 140. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

Input 102 includes various sensors and electrodes providing signals to processing and control 104 for detecting cardiac events. Input 102 is shown to include two ECG sensing electrode vectors 112 and 114 and an activity sensor 116. In alternative embodiments, one or more ECG and/or intracardiac EGM sensing vectors may provide cardiac electrical signals as input to processing and control 104. Activity sensor 116 is used in a cardiac event detection process, as will be further described below, for reducing the likelihood of a cardiac signal being classified as a treatable rhythm in the presence of motion artifact or muscle noise interference. Other physiological sensors may be included in alternative embodiments for providing additional signals used to detect arrhythmias or monitoring other patient conditions.

A "treatable" rhythm, as used herein, refers to any tachycardia that is ventricular in origin and can potentially be treated by delivering a therapy in the ventricles for terminating the ventricular tachycardia. A "non-treatable" rhythm is any rhythm with a relatively slow ventricular rate (below a ventricular tachycardia rate) and any tachycardia that is supraventricular in origin. Delivering a therapy, which may be anti-tachycardia pacing, cardioversion shock or defibrillation shock, only in the ventricular chambers frequently does not resolve a supraventricular tachycardia. The criteria applied to a cardiac signal for classifying the signal as a treatable rhythm may vary between embodiments but will typically involve analysis of RR intervals and/or analysis of the QRS waveform morphology.

The activity sensor 116 is typically located in the ICD housing or connector block. In SubQ devices, the activity sensor 116 is subjected to similar motion caused by patient activity as the ECG sensing array. As such, the methods described herein for using an activity sensor signal to reduce the likelihood of an ECG signal being classified as a treatable rhythm in the presence of patient activity or muscle noise can be particularly useful in SubQ devices.

Processing and control module 104, also referred to herein as "controller", includes a buffer 115 which stores an n-second segment of each of the ECG signals 112 and 114. An R-wave detector 118 receives both ECG1 and ECG2 signals 112 and 114 for sensing R-waves and determining RR intervals. An ECG morphology analysis module 120 receives inputs from both of the buffered n-segment ECG1 112 and ECG2 114 signals from buffer 115. Practice of the methods employing an activity sensor signal described herein, however, do not necessarily require the use of two ECG signals. In other embodiments, one or more ECG or EGM signals, collectively referred to herein as "cardiac signals", may be received by R-wave detector 118 and/or morphology analysis module 120.

Segment classification module 126 classifies each cardiac signal segment as "treatable" or "non-treatable" based on R-wave intervals received from R-wave detector 118 and morphology analyzer 120. Segment classification module 126 may employ the methods generally disclosed in U.S. patent application Ser. No. 11/557,597 for classifying an ECG segment as treatable or non-treatable. The '597 application is incorporated herein by reference in its entirety.

Segment classification module 126 determines a final segment classification using input from activity sensor 116. An activity count module 122 determines an activity level count (ALC) from the input signal from activity sensor 116. The ALC is provided to histogram 124 for generating ALC histograms and accumulative ALC histograms as will be further described below. The histogram data is used by an activity threshold analyzer 125 for use in evaluating and establishing an ALC threshold.

For each n-second cardiac signal segment that is initially classified as a "treatable" rhythm segment based on cardiac signal analysis, segment classification 126 receives a current ALC from activity count 122 and compares the current activity count associated with the initially-classified treatable segment to the ALC threshold for determining a final classification of the n-second segment. When the ALC is greater than the threshold, segment classification 126 reclassifies the treatable rhythm segment as a non-treatable rhythm segment to reduce the likelihood of shock (or other unneeded therapy) delivery due to false detection of a treatable rhythm in the presence of activity-induced noise.

An event detector 128 detects a treatable cardiac event when a required number of cardiac signal segments are classified as treatable. The therapy control module 130 responds to the detection of a treatable cardiac event by controlling high voltage (HV) shock pulse generator 132 or pacing pulse generator 134 to deliver a therapy according to the type of cardiac event detected and a programmed therapy delivery menu. In response to detecting a shockable rhythm, such as a fast VT or VF, HV shock pulse generator 132 is controlled to deliver a cardioversion/defibrillation shock using high voltage electrodes 136. Pacing pulse generator 134 is used to deliver pacing pulses using low voltage (LV) electrodes 138 as needed, e.g., during post-shock recovery, for anti-tachycardia pacing, or bradycardia pacing. It is recognized that in some embodiments, any of the HV electrodes 136 and LV electrodes 138 in output 108 may also be used as sensing electrodes in input 102.

ICD 100 includes telemetry circuit 140 capable of bidirectional communication with an external programmer 20 (shown in FIG. 1). Uplink telemetry allows device status and diagnostic/event data to be sent to external programmer 20 for review by the patient's physician. Downlink telemetry allows the external programmer 20 via physician control to allow the programming of ICD function and the optimization of the detection and therapy for a specific patient.

Telemetry circuit 140 is used to transmit ALC data to an external programmer. ALC histogram data may be displayed by the programmer or another external device to a clinician or other user for review. The displayed ALC data can be used in a semi-automatic method for selecting an ALC threshold and evaluating the impact of the ALC threshold on treatable cardiac event detection. Event detector 128 stores detected treatable cardiac event episodes, and the episode data can also be transmitted to an external device for review by a clinician.

ALC data stored in conjunction with ECG segments leading up to cardiac event detection may be included in the episode data. The ALC data used by segment classification 126 when ECG segments were classified as treatable segments (to either reclassify ECG segments as "non-treatable" segments or to maintain the treatable segment classification) may be combined with episode data for display and review by a clinician.

Figure 4:
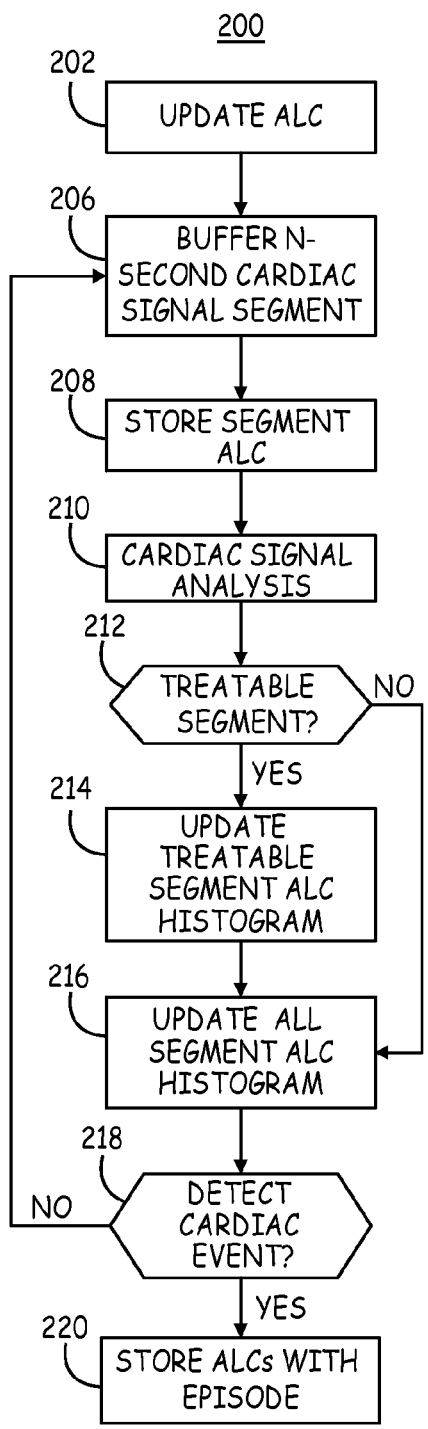
FIG. 4 is a flow chart of a method for acquiring activity level count (ALC) data for use in setting an ALC threshold.

FIG. 4 is a flow chart 200 of a method for acquiring ALC data for use in setting an ALC threshold. Flow chart 200 and other flow charts presented herein are intended to illustrate the functional operation of the device, and should not be construed as reflective of a specific form of software or hardware necessary to practice the methods described. It is believed that the particular form of software will be determined primarily by the particular system architecture employed in the device and by the particular detection and therapy delivery methodologies employed by the device. Providing software to accomplish the described functionality in the context of any modern ICD, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EPROM, EEPROM, flash memory, and the like. The instructions may be implemented as one or more software modules, which may be executed by themselves or in combination with other software.

The method shown in flow chart 200 may be performed beginning from the time of ICD implantation until a later time when enough ALC data has been gathered to establish an ALC threshold based on the patient's own ALC data. This data collection period may be for several days, weeks or months, or until the first patient follow-up, which may be in an office or a remote patient follow-up. After establishing an initial threshold, the collection of ALC data as will be described in conjunction with FIG. 4 may continue to allow adjustment of the ALC threshold as needed over time with changing patient activity patterns.

During an initial data acquisition period when method 200 is performed to set the ALC threshold based on the patient's own ALC data, a nominal ALC threshold may optionally be set based on clinical data or prior knowledge of a patient's typical activities of daily living. The nominal threshold may be used during cardiac event detection. An individualized threshold selected for a given patient based on ALC histogram data accumulated from the patient, however, is believed to provide the greatest improvement in treatable cardiac event detection specificity while maintaining high sensitivity.

At block 202, an ALC is updated according to an activity monitoring algorithm. The ALC may be acquired and updated according to numerous possible methods. In one embodiment, a weighted ALC is acquired over a six second interval which is updated every 2 seconds. The ALC may be obtained according to methods generally described in U.S. Pat. No. 6,449,508 (Sheldon, et. al), hereby incorporated herein by reference in its entirety. Updating of the ALC may be enabled to occur continuously beginning from the time of device implant such that ALCs can be updated throughout time.

At block 206 an n-second segment of the cardiac signal is buffered. As described above, two or more ECG and/or EGM signals may be buffered to obtain cardiac signal segments. For each n-second segment, a corresponding ALC is stored at block 208. The ALC stored in relation to a particular n-second segment may be the most recently-updated ALC occurring prior to the endpoint of the signal segment, the earliest ALC occurring within the signal segment, the earliest updated ALC after the signal segment, or another ALC updated in close temporal relation to the n-second segment.

Depending on the duration of the n-second segment and the frequency of updating an ALC, the ALC may be updated more than once during a signal segment or not at all during a given cardiac signal segment. As such, the updated ALC stored in conjunction with a given cardiac signal segment may be selected as an ALC occurring closest in time to a starting point, an endpoint or a midpoint of the n-second segment. Other ALC sampling methods for storing an ALC in relation to a n-second cardiac signal segment may include averaging two or more ALCs occurring during, immediately prior to, and/or immediately following the signal segment.

At block 210, each cardiac signal segment is analyzed to determine if the segment represents a treatable rhythm at decision block 212. If the segment is not classified as a treatable rhythm, the process advances to block 216. The current ALC stored in conjunction with the current n-second segment is used to adjust a histogram bin counter in an "all segment" ALC histogram. The histogram bin counter corresponding to the value of the ALC is increased by one count independent of any current or future rhythm classification of the segment. The all segment ALC histogram provides a count of all of the ALCs, in respective histogram bins, so that the accumulative amount of time that a patient exhibits activity at or above a particular activity level can be determined.

If the cardiac signal segment is classified as "treatable" at block 212 based on cardiac signal analysis, the ALC stored in conjunction with the current n-second segment is counted in a treatable segment ALC histogram at block 214. The treatable segment ALC histogram provides a count of all ALCs, in respective histogram bins, that the patient exhibits during time segments that the cardiac signal is classified as a treatable rhythm based on cardiac signal analysis.

While methods described herein refer generally to "treatable" cardiac signal segment classifications and the detection of "treatable" cardiac events, it is contemplated that an ALC threshold in a cardiac event detection algorithm is applied to reduce the number of unnecessary shock therapies in particular. In this case, a treatable segment ALC histogram may be used to store the ALCs associated with cardiac signal segments specifically classifieds as "shockable" segments only and exclude other signal segments associated with rhythms that are treated with anti-tachycardia pacing therapies. A shockable segment classification is associated with a rhythm that, if detected, is treated with a cardioversion or defibrillation shock, such as fast VT and VF. Other types of "treatable rhythms" may include rhythms that are first treated with anti-tachycardia pacing therapy, such as a relatively slower or hemodynamically stable VT. As such, in various embodiments, "treatable" may refer to "shockable" only, or more inclusively as any rhythm that, if detected, will result in any shock or anti-tachycardia therapy being delivered.

If more than one cardiac signal is being buffered and analyzed for each n-second segment, such as ECG1 and ECG2 as shown in FIG. 3, an ALC is counted in the treatable segment ALC histogram for each cardiac signal segment classified as treatable, regardless if the segments are buffered over the same n-second period. In other words, if both ECG1 and ECG2 shown in FIG. 3 are classified as treatable for a given n-second segment, the ALC stored in relation to the n-second segment is counted twice in the treatable segment ALC histogram. A histogram bin counter corresponding to the stored ALC will be increased by two at block 214. If only one of ECG1 and ECG2 for the current n-second segment is classified as treatable, the corresponding treatable segment ALC histogram bin counter will be increased by one at block 214.

Additionally, the ALC stored in conjunction with the current treatable signal segment is counted in the all segment ALC histogram at block 216. The histogram bins for the all segment ALC histogram and the treatable segment ALC histogram may be defined in the same way so that comparisons can be made between data acquired in the treatable segment ALC histogram and in the all segment ALC histogram.

If neither ECG1 nor ECG2 are classified as treatable for the n-second segment, the treatable segment ALC histogram is unchanged. A histogram bin counter corresponding to the stored ALC in the all segment ALC histogram is increased by one at block 216. The all segment ALC histogram is incremented once for each n-second time segment regardless of its classification based on cardiac signal classification.

The treatable segment ALC histogram may be incremented once, twice or not at all for a given n-second segment depending on the classifications resulting from the separate analysis of the two cardiac signal sensing vectors as described above. This equal but separate treatment of the two different sensing vector signals in adjusting a treatable segment ALC histogram is used because different sensing vectors can be affected or corrupted in different ways by the same activity for a given n-second segment. This difference in noise corruption or motion artifact between different sensing vectors can result in different classifications of the two cardiac signals for the same n-second time segment. For example, two different ECG sensing vectors may be selected to include a short bipole vector, such as a bipole formed by two electrodes along the ICD housing and a relatively larger bipole having greater inter-electrode separation distance, such as a bipole formed from one electrode on the ICD housing and a second electrode on a subcutaneous lead tunneled away from the ICD. In this illustrative example, the short bipole vector can be corrupted by chest muscle noise or motion artifact and the second larger bipole may be less affected by the same activity.

In another embodiment, separate ALC histograms may be assigned to each cardiac signal sensing vector for counting ALCs associated with treatable signal segments. The ALC for each n-second segment is counted separately for each sensing vector in separate treatable ALC histograms when a treatable segment classification occurs. Separate treatable segment ALC histograms for each cardiac signal sensing vector may facilitate selection of sensing vectors that yield the greatest separation between correctly classified treatable segments and segments classified as treatable due to muscle noise or motion artifact. Separate treatable ALC histograms may additionally be useful in selecting cardiac signal sensing vectors for use in cardiac event detection that are the least affected by muscle noise or motion artifact presented most often in association with an individual patient's typical activity patterns.

If the number of cardiac signal segments classified as treatable reaches a detection threshold at decision block 218, a cardiac event is detected as a treatable episode. A therapy is delivered according to programmed ICD therapy regimes. The treatable episode is stored in ICD memory at block 220 along with the ALCs stored for all or at least a portion of the n-second segments leading up to episode detection and/or during the episode.

If cardiac event detection criteria are not satisfied at block 218, the process returns to block 206 and continues to analyze the n-second cardiac signal segments. ALCs continue to be updated throughout and ALCs stored in relation to each n-second segment are used to adjust bin counters in the treatable and all segment ALC histograms as described above.

Figure 5:
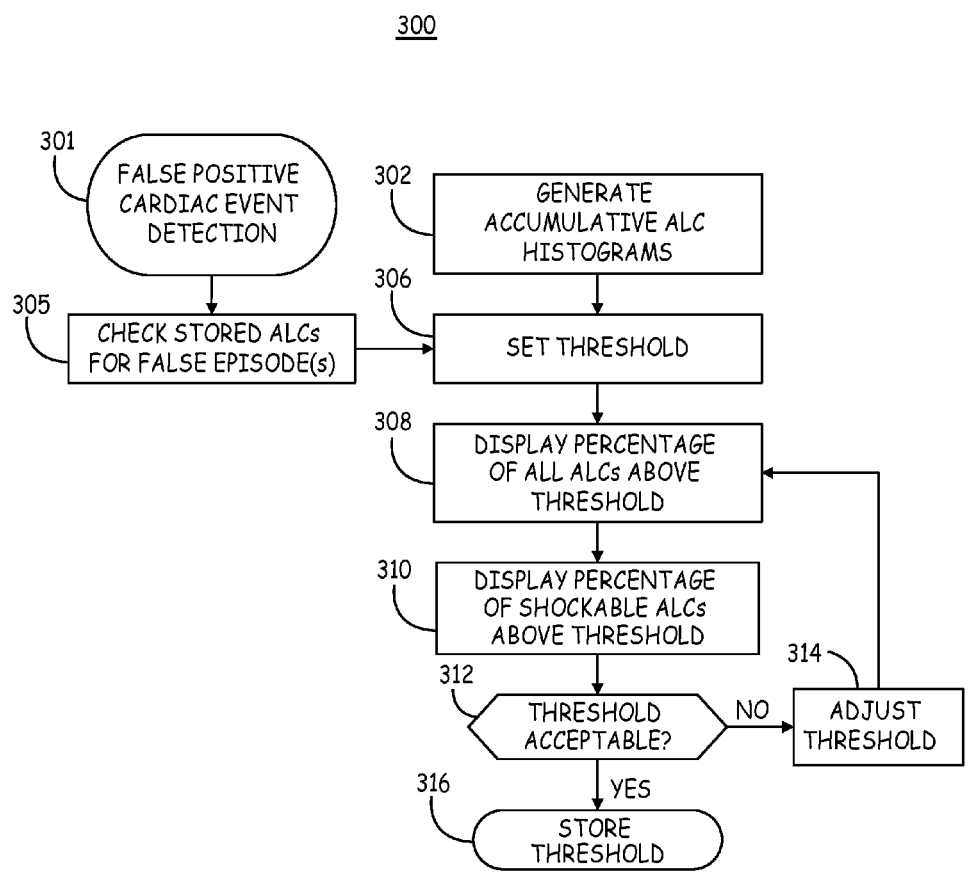
FIG. 5 is a flow chart of one method for setting an ALC threshold for use in a cardiac event detection algorithm.

FIG. 5 is a flow chart 300 of one method for setting an ALC threshold for use in a cardiac event detection algorithm. After acquiring ALC histogram data for a period of time, an ALC threshold is established, in an automatic or semi-automatic method using the ALC data. The ALC threshold is used to reclassify cardiac signal segments as non-treatable when interval and morphology-based analysis of the cardiac signal results in a treatable segment classification and the ALC stored for the treatable segment exceeds the ALC threshold.

At block 302, accumulative ALC histograms are generated from the treatable and all segment ALC histograms. An accumulative ALC histogram provides the percentage of time (or time segments) that a patient exhibits an ALC that is equal to or above a given ALC.

Figure 6A:
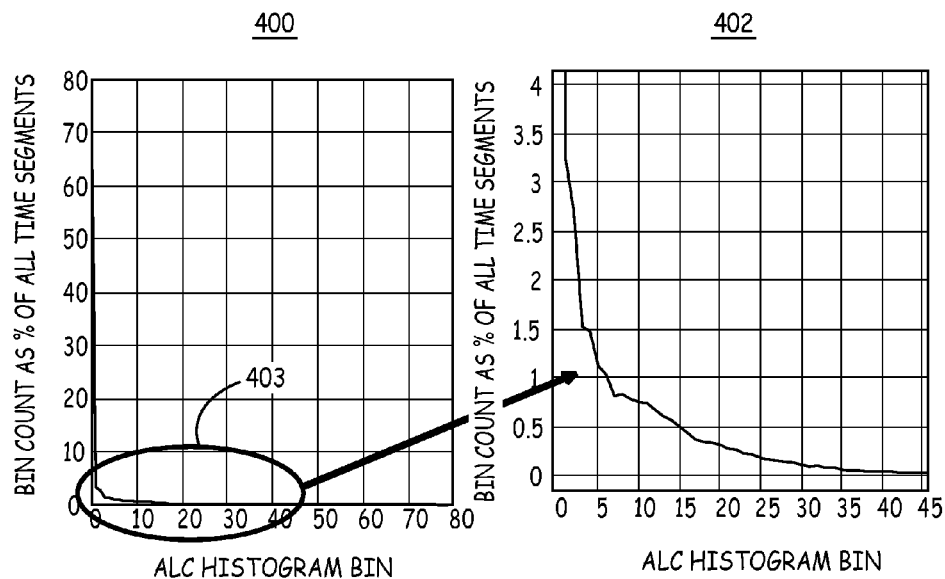
FIG. 6A is a plot of an ALC histogram and an enlarged view of a portion of the plot.

FIG. 6A is a plot 400 of all segment ALC histogram data and an enlarged view 402 of a portion of the plot 400. In the left panel of FIG. 6A, the ALC histogram data is plotted as a curve showing the individual histogram bin counts for each ALC as a percentage of the total number of all histogram bin counts combined. The encircled portion 403 is shown enlarged in the right panel 402 of FIG. 6A. As can be seen in the enlarged portion, for example, the patient exhibited an ALC of 5 slightly more than 1% of the time. In other words, the bin count for an ALC of 5 was approximately 1% of the total of all bin counts. The patient exhibited an ALC of 15 about 0.5% of the time.

Figure 6B:
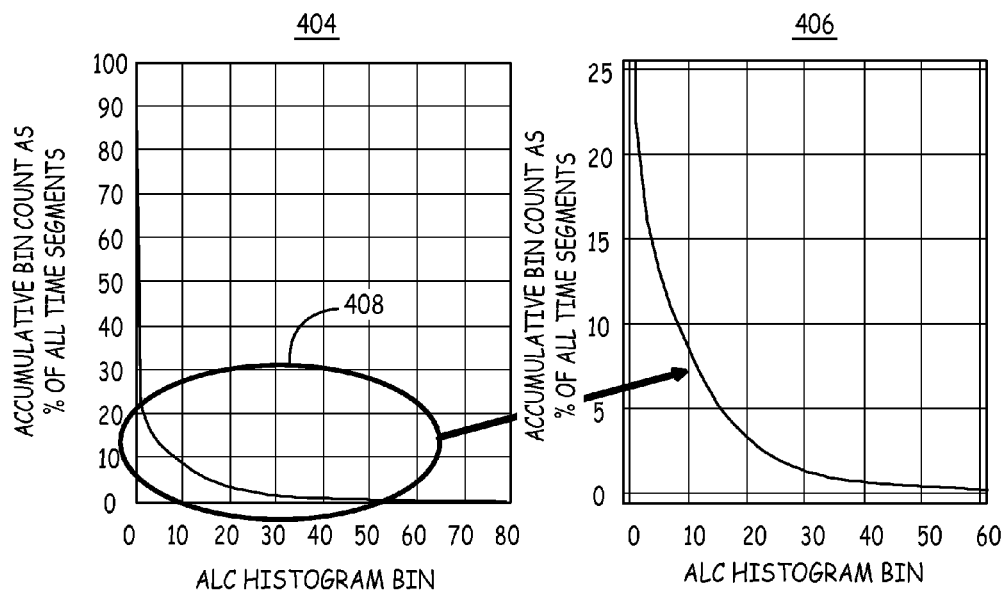
FIG. 6B is a plot of an accumulative ALC histogram generated using the data from the ALC histogram of FIG. 6A and an enlarged view of a portion of the plot.

FIG. 6B is a plot 404 of an accumulative ALC histogram generated using the data from the ALC histogram of FIG. 6A. The right panel of FIG. 6B is an enlarged view 406 of the encircled portion 408 of the plot 404 in the left panel. To obtain an accumulative ALC histogram plot 404, the value of each histogram bin is summed with the counts of each of the histogram bins assigned to ALCs greater than the given histogram bin. The sum of all bin counts at or higher than a given ALC provides an accumulative bin count for the given ALC. For example, the bin counts equal to or greater than an ALC of 15 in FIG. 6A are summed to obtain a combined or accumulative bin count that corresponds to the count of all ALCs stored in the all segment histogram equal to or greater than 15.

The accumulative bin count can then be expressed as a percentage of the total of all histogram bin counts combined (i.e., the total number of n-second segments counted by the histogram). An accumulative percentage of time (or time segments) that a patient exhibits an ALC equal to or greater than a given ALC is plotted as a function of the ALC, as shown in plot 404. As seen in the enlarged view 406, the patient exhibits an ALC of 15 or higher approximately 5% of the time. The patient exhibits an ALC of 10 or higher approximately 8% of the time. This accumulative ALC histogram can therefore be used to tailor an ALC threshold to a specific patient based on the history of the patient's accumulative activity data and an understanding of how much of the time a patient spends at or above any given ALC.

Alternative methods for selecting an ALC threshold may involve setting the threshold as a percentage of an overall average or baseline activity level of the patient. These alternative methods do not take into account how much time a patient may actually spend at or above the selected threshold. A threshold selected based as a percentage of a baseline activity or an overall average activity level may result in cardiac signal segments being reclassified too often or not often enough, depending on the activity of the particular patient. Improvement in the specificity (while maintaining high sensitivity) of treatable cardiac event detection may not be achieved without taking into consideration both the range of activity level and the accumulative amount of time a patient exhibits different activity levels.

For example, a baseline ALC could be approximately equal in two different patients but one patient may perform higher levels of activity more often than the other patient. If the same ALC threshold is used in both patients based on their common baseline ALC, a greater number of "treatable" ECG segments may be reclassified as non-treatable in the more active patient than in the less active patient. This reclassification may result in underdetection of treatable cardiac events in the active patient. Conversely, treatable segments that should be reclassified as non-treatable because of activity-induced artifact may cause over-detection of treatable cardiac events (i.e. some false detections) in the less active patient.

Referring again to FIG. 5, a threshold is set at block 306 based on the accumulative ALC histogram data. The threshold may be set based on a combination of all segment and treatable segment ALC histogram data. If the amount of treatable ALC histogram data is limited, the threshold may be set based on the all segment ALC histogram data.

If any false positive treatable cardiac event detections are identified by a user at a patient follow-up session as indicated at block 301, the ALCs stored for the falsely detected episode may be examined at block 305. An ALC stored during the falsely detected episode may be used in setting the ALC threshold at block 306. The threshold may be selected by a clinician or other user at block 306 based on an ALC during a falsely detected episode, based on viewing the accumulative ALC histogram, or a combination of both.

In one embodiment, a histogram of ALCs for each n-second segment leading up to the time of detection, or summary ALC data such as a minimum, maximum, median and/or mean ALC for the n-second segments that contributed to a cardiac event detection, may be stored and displayed with episode data. This data will further separate and distinguish ALCs that occur during n-second segments leading up to falsely detected episodes from those leading up to true cardiac event detection. An optimal activity threshold would be a value less than a majority of the ALCs stored during treatable segments leading up to false cardiac event detection and greater than a majority of the ALCs stored during the treatable segments leading up to the true cardiac event detection. As such, the ALCs stored for treatable segments resulting in both false and true cardiac event detections may be examined at block 305 to provide information for setting the ALC threshold at block 306.

The threshold at block 306 may alternatively be set automatically based on an ALC stored during a detected episode that has been flagged by a user as a falsely detected episode. A user may review stored episodes and flag any episodes that are not true cardiac event episodes. The flagged episode data may be downlinked to the ICD for use in automatically setting the ALC threshold. The ALC threshold may alternatively be set automatically at a level above which a patient spends a predetermined percentage of time, e.g. approximately 2%, 5%, 10%, or another selected percentage of time.

Figure 7:
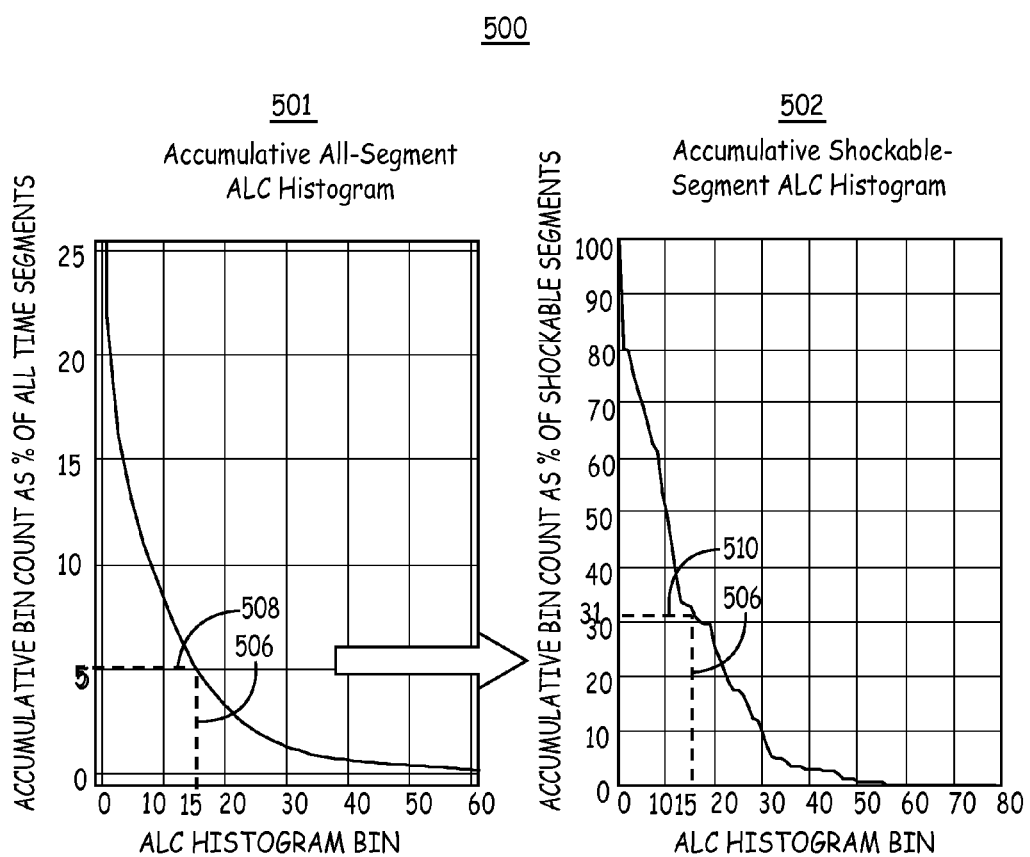
FIG. 7 is a display of an accumulative all cardiac signal segment ALC histogram plot and an accumulative treatable cardiac signal segment ALC histogram plot.

At blocks 308 and 310, respectively, and as shown in FIG. 7, the accumulative all segment ALC histogram plot 501 and the accumulative treatable segment ALC histogram plot 502 may be used to generate a display 500 for review by a user. In display 500, the accumulative all segment ALC histogram plot 501 shows the percentage of time (or percentage of all time segments) that a patient spends at or above a given ALC plotted as a function of the ALC. For example, if an ALC of 15 is selected as a threshold 506, the plot 501 shows that the patient exhibits an ALC of 15 or higher 5% of the time. As such, a user is aware that at or above this threshold, the patient spends a relatively small amount of time based on the accumulative histogram count for the given threshold of 15 summed with all histogram bin counts for an ALC greater than 15. The patient spends approximately 95% of his/her time below an ALC of 15.

The accumulative treatable segment ALC histogram plot 502 shows what percentage of treatable segments the patient exhibits an ALC at or above a given threshold 506. In this example, the patient exhibits an ALC at or above 15 for approximately 31% of the treatable time segments. As such, an ALC threshold of 15 could result in nearly one-third of all treatable segments being reclassified as non-treatable. If a clinician finds these percentages 508 and 510 acceptable, the threshold 506 is accepted at block 312 of FIG. 5. The threshold is stored at block 316 for use during a cardiac event detection algorithm, as will be further described below.

The display 500 may be a graphical user interface that allows a user to select different thresholds. Upon selection of a threshold, the percentage of time (or percentage of n-second segments) that the patient is at or above the threshold is plotted for all n-second segments (plot 501) and for treatable segments only (plot 502). The display 500 may therefore be used to initially select a threshold and then make adjustments if needed until the threshold is acceptable.

In an automated algorithm, the ICD may select a threshold that corresponds to a targeted percentage of all time segments and/or a targeted percentage of treatable time segments. For example, a threshold may be selected as an ALC at or above which 2% to 5% of all time segments occur and 20% to 30% of all treatable time segments occur. A threshold meeting these criteria is selected and stored as the ALC threshold.

In the example of FIG. 7, an ALC threshold range between approximately 15 and 28 corresponds to 2% to 5% of all time segments as can be observed in plot 501. In plot 502, an ALC between approximately 18 and 23 corresponds to approximately 20% to 30% of all treatable time segments. As such a threshold in the range of approximately 18 to 23, e.g. a threshold of 20, meets both a percentage criterion applied to all time segments and a percentage criterion applied to all treatable time segments.

If stored episodes have been flagged as falsely detected episodes by a user, the percentage of false episodes out of all detected episodes may be used as a guide for the percentage of all treatable segments that are desired to be reclassified as non-treatable segments. This percentage may be used as an approximate boundary for setting the threshold in plot 502 of FIG. 7. For example, if approximately 20% of all the treatable cardiac event episodes are flagged as false cardiac event detections, and are associated with a relatively high ALC, a user may select a threshold that corresponds to 20% of all treatable time segments. In the example of FIG. 7, about 20% of all treatable segments occur with an ALC of approximately 23 or higher. As such an ALC threshold of approximately 23 may be used to reduce the number of falsely detected treatable cardiac events.

Referring again to FIG. 5, the threshold may be considered unacceptable at block 312 if a high percentage of segments are at or above the threshold. In some embodiments, acceptable maximum percentages of the all rhythm segments and/or the treatable segments may be defined to prevent a threshold from being set too low. If the threshold results in a high percentage of time segments at or above the threshold, the threshold may be adjusted higher at block 314 to prevent treatable segments from being reclassified too frequently. Furthermore, a lower ALC limit (and/or an upper limit on the percentage of time segments at or above the ALC threshold) may be defined to prevent the ALC threshold from being set too low. For example, an ALC lower limit of 10 may be set in the illustrative embodiment shown. ALC limits (or limits applied to the percentage of time segments at or above the ALC threshold) may be defined individually for a given patient or set nominally in the ICD.

A threshold may also be unacceptable at block 312 if the percentage of treatable segments at or above the threshold is too low. The threshold may not effectively reduce the likelihood of shock delivery due to a falsely detected cardiac events caused by motion artifact. The threshold can be adjusted at block 314 until the threshold is considered acceptable and stored at block 316.

Figure 8:
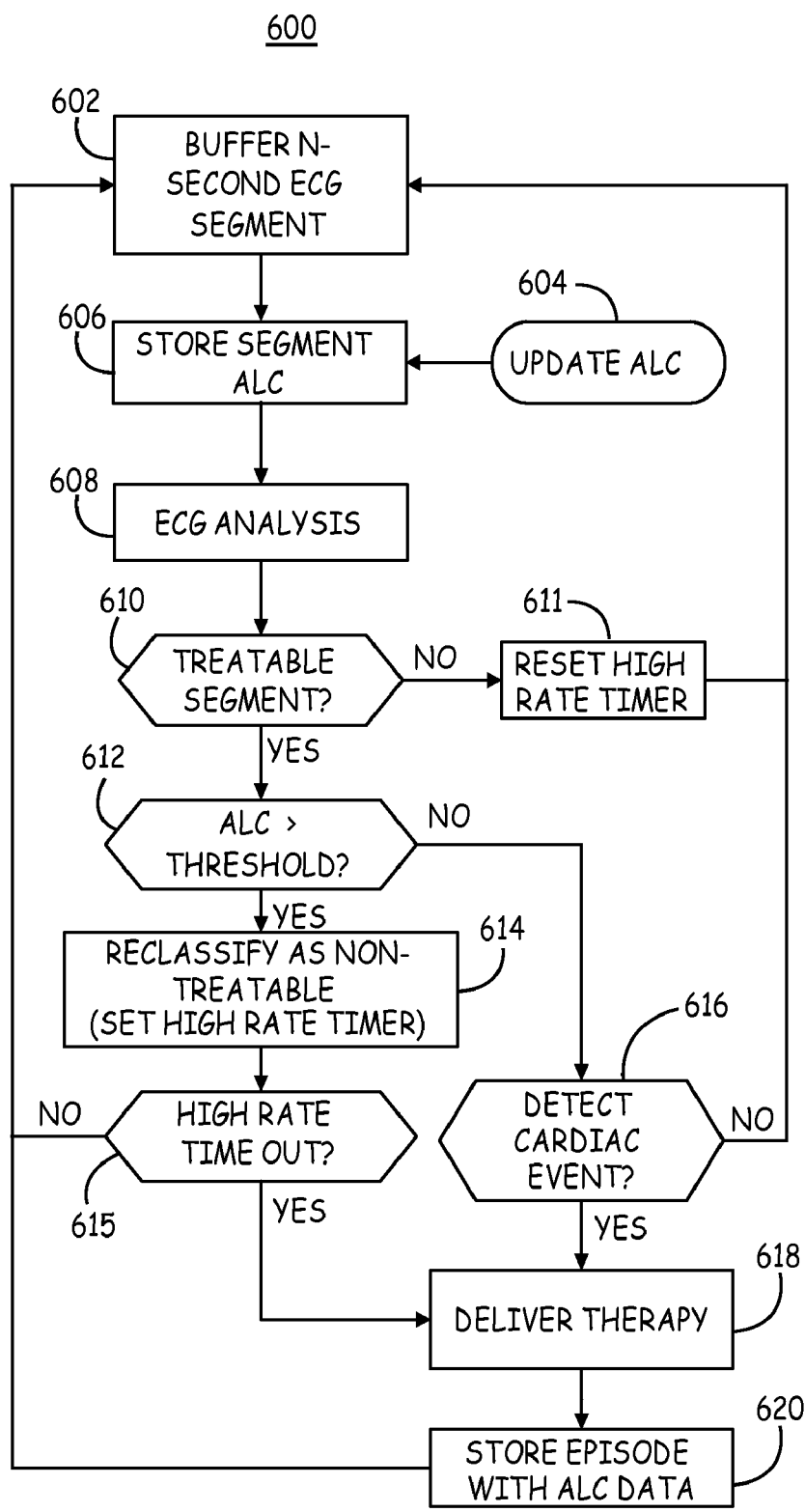
FIG. 8 is a flow chart of a method for detecting a cardiac event using an ALC threshold according to one embodiment.

FIG. 8 is a flow chart 600 of a method for detecting a cardiac event according to one embodiment. At block 602, an n-second cardiac signal segment (e.g. ECG signal segment) is buffered for RR interval and morphology analysis. As mentioned previously, an n-second segment from one or more ECG and/or EGM sensing vectors may be obtained contemporaneously. At block 606, an updated ALC occurring in timed relation to the buffered cardiac signal segment(s) is stored. The ALC is updated regularly at block 604 according to an activity monitoring algorithm such that an ALC that corresponds to the patient activity at the same time (or approximately the same time) as the n-second cardiac signal segment can be stored.

If the cardiac signal analysis performed at block 608 results in a non-treatable rhythm classification at block 610 (negative result), the process returns to block 602 to acquire the next n-second cardiac signal segment. The ALC is not used in classifying the segment when the interval and/or morphology-based analysis of the cardiac signal results in a non-treatable rhythm classification.

In some embodiments, a high rate timer is used to set a maximum time limit that a high cardiac rate detected by cardiac signal analysis may exist without delivering a therapy. If a high rate timer is running, it may be reset to zero at block 611 in response to classifying one or more segments as a non-treatable segments based on cardiac signal analysis alone. One or more non-treatable segments, based on interval and/or morphology analysis, represents a break in a high rate rhythm.

If the cardiac signal analysis at block 608 results in a treatable segment classification at decision block 610, the ALC stored for the current n-second segment is compared to the ALC threshold at block 612. When the ALC associated with the current n-second segment is greater than the threshold, the n-second segment is reclassified as non-treatable at block 614. The method returns to block 602 to acquire the next n-second segment. A cardiac event will not be detected in response to the current n-second segment.

In some embodiments, an optional high rate timer is set at block 614 in response to a segment, or a grouping of n out of m segments, being reclassified as non-treatable at block 514. If a high rate, as determined from cardiac signal analysis, persists for a predetermined high rate time out interval as determined at block 615, a shock therapy (or other arrhythmia therapy) may be delivered at block 618 even though one or more cardiac signal segments were reclassified as non-treatable during the predetermined time limit. The high rate timer is an optional safety measure used to prevent a fast tachycardia from going untreated due to ALC-based reclassifications of n-second segments.

As such, if a high rate timer is not already running upon reclassifying a signal segment at block 614, the high rate timer may be started when a required number of signal segments are reclassified as non-treatable. In alternative embodiments, the high rate timer may be started in response to detecting a high heart rate and may be reset to zero only when the heart rate falls below a predetermined heart rate threshold. The high rate timer may be set between approximately 30 seconds and two minutes in some embodiments.

In an alternative embodiment, the high rate timer may be embodied as an adjustment to the cardiac event detection criteria. In this case, rather than setting a timer when one or more treatable segments are reclassified as non-treatable based on an ALC threshold, the number of treatable segment classifications required to detect a cardiac event may be reduced.

For example, if the number of treatable segments based on ECG analysis reaches a cardiac event detection threshold, for example 5 out of the most recent 8 n-second segments are treatable based on ECG, but one or more of those segments are reclassified as non-treatable due to the ALC exceeding the ALC threshold, the cardiac event detection criterion applied to future segments may be reduced to 3 treatable segments out of 5 n-second segments. If this lower detection criterion is met after analyzing n-second time segments occurring after the detection criterion adjustment, cardiac event detection is made and a therapy is delivered as needed.

In still other embodiments, a high rate timer may be embodied as a combination of an adjustment to event detection criterion and a time out interval. For example, the detection criterion is adjusted to a lower number of treatable segments out of a given number of n-second segments in response to one or more treatable segments being reclassified. A time out interval may also be set in response to one or more treatable segments being reclassified. As long as the lower event detection criterion remains met, the timer will continue to advance toward the time out interval. Upon expiration of the time out interval, the cardiac event is detected. If the lower detection criterion is no longer met before the time out interval expires, the high rate timer will be reset. The time out interval will be set to a starting time and the detection criterion will be reset to the higher number of treatable segments out of a given number of segments.

If the ALC does not exceed the threshold at block 612, the treatable segment classification stands. The detection method proceeds to block 616 to determine if cardiac event detection criteria are met. Detection criteria may require, for example, five out of eight of the most recent n-second segments be classified as treatable, though other detection criteria may be defined. When cardiac event detection criteria are met, a shock therapy (or other therapy as programmed in the ICD) is delivered at block 618. The detected episode is stored at block 620 with ALC data. The ALC data allows segment classifications and reclassifications and corresponding ALCs to be reviewed for verification of proper cardiac event detection and further optimization of the ALC threshold if necessary.

While particular embodiments have been shown and described, modifications may be made. It is therefore intended in the appended claims to cover all such changes and modifications, which fall within the true spirit and scope of the disclosed methods and apparatus.

We claim:

1. A method for detecting a cardiac event in a patient, comprising:
   determining an activity level count from an activity sensor signal for each of a plurality of time segments;
   storing an activity level count for each of the plurality of time segments in a histogram;
   accumulating the stored activity level counts to determine a percentage of time segments having an activity level count above a given activity level count;
   establishing an activity level count threshold in response to the accumulated activity level counts;
   sensing a cardiac signal from a plurality of electrodes for each of the plurality of time segments;
   classifying the cardiac signal for each of the plurality of time segments as one of a treatable segment and a non-treatable segment;
   comparing a stored activity level for a given one of the plurality of time segments to the activity level count threshold in response to classifying a treatable segment;
   reclassifying the treatable segment as a non-treatable segment if the stored activity level for the given one of the plurality of time segments is greater than the activity level count threshold; and
   detecting the cardiac event in response to a treatable segment not being reclassified.

2. The method of claim 1 wherein storing the activity level count for each of the plurality of time segments in a histogram comprises:
   storing the activity level count for a current one of the plurality of time segments in a first histogram; and
   storing the activity level count for the current one of the plurality of time segments in a second histogram in response to the current one of the plurality of time segments being classified a treatable segment.

3. The method of claim 2 wherein establishing the activity level count threshold comprises determining a percentage of treatable segments in the second histogram having an activity level count above the threshold.

4. The method of claim 1 further comprising storing an activity level count corresponding to the detected cardiac event.

5. The method of claim 4 further comprising determining whether the detected cardiac event is a falsely detected event; and
   adjusting the activity level count threshold in response to the falsely detected event and the stored activity level count.

6. The method of claim 1 further comprising establishing one of a minimum activity level count threshold and a maximum percentage of time segments having an activity level count above the established threshold.

7. The method of claim 3 wherein accumulating activity level counts comprises:
   accumulating activity level counts from the first histogram to determine a percentage of the plurality of time segments having an activity level count at or above a given activity level count, and
   accumulating activity level counts from the second histogram to determine a percentage of treatable segments having an activity level count at or above a given activity level count, and further comprising
   displaying the accumulated activity level counts from the first histogram, the accumulated activity level counts from the second histogram, and the established threshold.

8. The method of claim 1 wherein the accumulated activity level counts used to determine a percentage of time segments above a given activity level correspond to treatable time segments.

9. The method of claim 8 further comprising determining a percentage of previously detected cardiac events being falsely detected cardiac events;
   wherein establishing the threshold comprises identifying an accumulated activity level count corresponding to a percentage of treatable time segments at or above the threshold approximately equaling the percentage of falsely detected cardiac events.

10. The method of claim 1 further comprising:
    setting a high rate time out interval in response to a treatable segment being reclassified as a non-treatable segment; and
    detecting the cardiac event in response to the high rate time out interval expiring.

11. The method of claim 1 further comprising:
    establishing a threshold number of treatable segments not being reclassified as non-treatable segments required for detecting the cardiac event; and
    adjusting the threshold number in response to a treatable segment being reclassified as a non-treatable segment.

12. A medical device for detecting cardiac events, comprising:
    an activity sensor to sense a signal correlated to a level of patient activity;
    a plurality of electrodes to sense cardiac electrical signals; and
    a controller configured to:
    determine an activity level count from the activity sensor signal for each of a plurality of time segments;
    store an activity level count for each of the plurality of time segments in a histogram;
    accumulate the stored activity level counts to determine a percentage of time segments having an activity level count above a given activity level count;
    establish an activity level count threshold in response to the accumulated activity level counts;
    classify the cardiac signal for each of the plurality of time segments as one of a treatable segment and a non-treatable segment;
    compare a stored activity level for a given one of the plurality of time segments to the activity level count threshold in response to classifying a treatable segment; and
    reclassify the treatable segment as a non-treatable segment if the stored activity level for the given one of the plurality of time segments is greater than the activity level count threshold.

13. The device of claim 12 wherein the controller is further configured to store the activity level count for a current one of the plurality of time segments in a first histogram, and
    store the activity level count for the current one of the plurality of time segments in a second histogram in response to the current one of the plurality of time segments being classified a treatable segment.

14. The device of claim 13 wherein the controller is further configured to determine a percentage of treatable segments in the second histogram having an activity level count above the threshold.

15. The device of claim 12 wherein the controller is further configured to detect a cardiac event in response to the cardiac signal being classified as treatable, and store an activity level count corresponding to the detected cardiac event.

16. The device of claim 15 wherein the controller is further configured to receive data indicating that the detected cardiac event is a falsely detected event, and adjust the activity level count threshold in response to the falsely detected event and the stored activity level count.

17. The device of claim 12 wherein the controller is further configured to establish one of a minimum activity level count threshold and a maximum percentage of time segments having an activity level count above the established threshold.

18. The device of claim 13 wherein the controller is configured to accumulate activity level counts from the first histogram to determine a percentage the plurality of time segments having an activity level count at or above a given activity level count, and accumulate activity level counts from the second histogram to determine a percentage of treatable segments having an activity level count at or above a given activity level count, and wherein the controller is further configured to generate a display of the accumulated activity level counts from the first histogram, the accumulated activity level counts from the second histogram, and the established threshold.

19. The device of claim 12 wherein the accumulated activity level counts used to determine a percentage of time segments above a given activity level correspond to treatable time segments.

20. The device of claim 19 wherein the controller is further configured to determine a percentage of previously detected cardiac events being falsely detected cardiac events, and establish the threshold by identifying an accumulated activity level count corresponding to a percentage of treatable time segments above the threshold approximately equaling the percentage of falsely detected cardiac events.

21. The device of claim 12 further comprising a therapy delivery module, wherein the controller is further configured to set a high rate timer in response to a treatable segment being reclassified as a non-treatable segment and control the therapy delivery module to delivery an arrhythmia therapy in response to the high rate timer expiring.

22. The device of claim 12 wherein the controller is further configured to store a threshold number of treatable segments not being reclassified as non-treatable segments required for detecting the cardiac event, and adjust the threshold number in response to a treatable segment being reclassified as a non-treatable segment.

23. A non-transient computer-readable medium storing a set of instructions that cause a medical device processor to:
    determine an activity level count from an activity sensor signal for each of a plurality of time segments;
    store an activity level count for each of the plurality of time segments in a histogram;
    accumulate the stored activity level counts to determine a percentage of time segments having an activity level count above a given activity level count;
    establish an activity level count threshold in response to the accumulated activity level counts;
    sense a cardiac signal from a plurality of electrodes for each of the plurality of time segments;
    classify the cardiac signal for each of the plurality of time segments as one of a treatable segment and a non-treatable segment;
    compare a stored activity level for a given one of the plurality of time segments to the activity level count threshold in response to classifying a treatable segment;
    reclassify the treatable segment as a non-treatable segment if the stored activity level for the given one of the plurality of time segments is greater than the activity level count threshold; and
    detect the cardiac event in response to a treatable segment not being reclassified.

* * * * *